US009498291B2

(12) United States Patent
Balaji et al.

(10) Patent No.: US 9,498,291 B2
(45) Date of Patent: Nov. 22, 2016

(54) TOUCH-FREE CATHETER USER INTERFACE CONTROLLER

(71) Applicant: Hansen Medical, Inc., Mountain View, CA (US)

(72) Inventors: Kamini Balaji, Mountain View, CA (US); Sean Paul Walker, Fremont, CA (US); Serena H. Wong, Mountain View, CA (US); June Park, Palo Alto, CA (US); Richard Henderson, Fremont, CA (US)

(73) Assignee: HANSEN MEDICAL, INC., Mountain View, CA (US)

( * ) Notice: Subject to any disclaimer, the term of this patent is extended or adjusted under 35 U.S.C. 154(b) by 923 days.

(21) Appl. No.: 13/833,482

(22) Filed: Mar. 15, 2013

(65) Prior Publication Data
US 2014/0276934 A1 Sep. 18, 2014

(51) Int. Cl.
*G06F 19/00* (2011.01)
*A61B 19/00* (2006.01)
*A61B 17/00* (2006.01)

(52) U.S. Cl.
CPC ........... *A61B 19/2203* (2013.01); *A61B 34/30* (2016.02); *A61B 34/37* (2016.02); *A61B 34/74* (2016.02); *A61B 2017/00212* (2013.01); *A61B 2017/00221* (2013.01); *A61B 2034/301* (2016.02)

(58) Field of Classification Search
CPC ... A61B 19/2203; A61B 5/103; A61B 5/117
USPC .............. 700/245, 257, 258; 606/1, 2, 5, 10, 606/13–16, 34, 41, 130, 139, 151, 153, 223, 606/232; 600/101, 433–435, 466, 585; 607/1, 88, 89; 623/13.13, 13.14, 17.16
See application file for complete search history.

(56) References Cited

U.S. PATENT DOCUMENTS

| | | | |
|---|---|---|---|
| 4,700,693 A | 10/1987 | Lia et al. |
| 5,398,691 A | 3/1995 | Martin et al. |
| 5,408,409 A | 4/1995 | Glassman et al. |
| 5,524,180 A | 6/1996 | Wang et al. |
| 5,631,973 A | 5/1997 | Green |
| 5,666,503 A | 9/1997 | Campanelli et al. |
| 5,713,946 A | 2/1998 | Ben-Haim |
| 5,749,362 A | 5/1998 | Funda et al. |
| 5,859,934 A | 1/1999 | Green |
| 5,876,325 A | 3/1999 | Mizuno et al. |
| 5,951,475 A | 9/1999 | Gueziec et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,591,239 B1 | 7/2003 | McCall et al. |

(Continued)

FOREIGN PATENT DOCUMENTS

WO 03086190 A1 10/2003

*Primary Examiner* — McDieunel Marc
(74) *Attorney, Agent, or Firm* — Dorsey & Whitney LLP; Scott M. Smith

(57) ABSTRACT

A command interpreter is in communication with a wireless controller. The command interpreter is configured to identify a reference location of the wireless controller, identify a second location of the wireless controller, and determine, based on the reference location and the second location, a sequence of instrument commands configured to adjust positioning of the instrument device.

13 Claims, 5 Drawing Sheets

(56) References Cited

U.S. PATENT DOCUMENTS

| | | | |
|---|---|---|---|
| 6,726,675 B1 | 4/2004 | Beyar | |
| 6,847,336 B1* | 1/2005 | Lemelson | A61B 1/00048 345/8 |
| 6,999,852 B2* | 2/2006 | Green | A61B 1/00193 348/E13.014 |
| 7,155,315 B2 | 12/2006 | Niemeyer et al. | |
| 7,259,652 B2 | 8/2007 | Wang et al. | |
| 7,395,249 B2 | 7/2008 | Wang et al. | |
| 7,543,588 B2 | 6/2009 | Wang et al. | |
| 7,594,925 B2 | 9/2009 | Danek et al. | |
| 8,041,413 B2* | 10/2011 | Barbagli | A61B 5/06 600/424 |
| 8,052,621 B2* | 11/2011 | Wallace | A61B 5/6885 600/587 |
| 8,343,171 B2 | 1/2013 | Farritor et al. | |
| 9,271,663 B2* | 3/2016 | Walker | A61B 5/061 |
| 2004/0106916 A1 | 6/2004 | Quaid et al. | |
| 2004/0176751 A1* | 9/2004 | Weitzner | A61B 17/0469 606/1 |
| 2006/0025676 A1 | 2/2006 | Viswanathan et al. | |
| 2006/0084945 A1* | 4/2006 | Moll | A61B 8/12 606/1 |
| 2006/0094956 A1* | 5/2006 | Viswanathan | A61B 19/22 600/431 |
| 2006/0156851 A1 | 7/2006 | Jacobsen et al. | |
| 2006/0293643 A1* | 12/2006 | Wallace | A61B 19/5244 606/1 |
| 2007/0083098 A1* | 4/2007 | Stern | A61B 1/00188 600/407 |
| 2008/0082109 A1* | 4/2008 | Moll | 606/130 |
| 2008/0243064 A1* | 10/2008 | Stahler | 604/95.01 |
| 2009/0012533 A1* | 1/2009 | Barbagli | A61B 19/22 606/130 |
| 2009/0024141 A1* | 1/2009 | Stahler | A61B 19/2203 606/130 |
| 2009/0137952 A1 | 5/2009 | Ramamurthy et al. | |
| 2009/0138025 A1* | 5/2009 | Stahler | 606/130 |
| 2010/0013764 A1 | 1/2010 | Gu et al. | |
| 2010/0121269 A1 | 5/2010 | Goldenberg et al. | |
| 2010/0280320 A1* | 11/2010 | Alvarez | A61B 17/00234 600/146 |
| 2010/0280449 A1* | 11/2010 | Alvarez | A61B 17/00234 604/95.04 |
| 2010/0280525 A1* | 11/2010 | Alvarez | A61B 17/00234 606/130 |
| 2010/0331856 A1* | 12/2010 | Carlson | A61B 1/00147 606/130 |
| 2011/0015484 A1* | 1/2011 | Alvarez | A61B 1/307 600/109 |
| 2011/0282140 A1 | 11/2011 | Itkowitz et al. | |
| 2011/0288561 A1 | 11/2011 | Devengenzo et al. | |
| 2011/0319815 A1* | 12/2011 | Roelle | A61B 1/00149 604/95.01 |
| 2012/0016291 A1* | 1/2012 | Hlavka | A61B 18/1492 604/21 |
| 2012/0071752 A1* | 3/2012 | Sewell | A61B 6/12 600/424 |
| 2012/0071891 A1 | 3/2012 | Itkowitz et al. | |
| 2012/0172666 A1 | 7/2012 | Lawrence et al. | |
| 2012/0278759 A1 | 11/2012 | Curl et al. | |
| 2012/0283819 A1 | 11/2012 | Taylor et al. | |
| 2013/0190741 A1* | 7/2013 | Moll | A61B 1/00082 606/13 |
| 2013/0317519 A1* | 11/2013 | Romo | 606/130 |
| 2014/0012286 A1* | 1/2014 | Lee | A61B 19/2203 606/130 |
| 2014/0277334 A1* | 9/2014 | Yu | A61B 19/2203 623/1.11 |
| 2015/0005785 A1* | 1/2015 | Olson | A61B 19/2203 606/130 |
| 2015/0100065 A1* | 4/2015 | Zinn | A61B 19/2203 606/130 |
| 2015/0374956 A1* | 12/2015 | Bogusky | A61M 25/0052 604/95.04 |

* cited by examiner

TOUCH-FREE CATHETER USER INTERFACE CONTROLLER

BACKGROUND

Minimally invasive surgery (MIS) systems may utilize flexible robotic catheters that are navigated in the bloodstream of a patient and visualized using X-rays. MIS devices and techniques have advanced to the point where an elongated catheter instrument is controllable by selectively operating tensioning control elements within the catheter instrument. In one example, four opposing directional control elements wend their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison.

MIS systems typically include controller devices having an assortment of controls to allow an operator to maneuver the catheter instrument as well as a guide wire guided by the catheter instrument. Some controller devices employ buttons dedicated to control the catheter instrument and a second set of buttons to control the guide wire. Other controller devices include a joystick type controller to control the catheter, often one-handed, and a separate set of button controls to control the guide wire. However, control systems for such instruments may be expensive, and may take up valuable real estate inside the operating room that may be otherwise used to store equipment, supplies, or provide for improved access to the patient.

SUMMARY

An exemplary device for controlling a medical instrument device may include a command interpreter in communication with a wireless controller. The command interpreter may be configured to identify a reference location of the wireless controller, identify a second location of the wireless controller, and determine, based on the reference location and the second location, a sequence of instrument commands configured to adjust positioning of the instrument device.

A system may include a wireless controller. The wireless controller may include a first body element including a location measurement device, a second body element including a second location measurement device and connected to the first body element by a flexible connection, and a wireless transmitter configured to provide location information from location measurement device and the second location measurement device. The system may further include a command interpreter in communication with the wireless controller, the command interpreter configured to identify a reference location of the wireless controller according to first location information received from the wireless controller, identify a second location of the wireless controller according to second location information received from the wireless controller, and determine, based on the reference location and the second location, a sequence of instrument commands configured to adjust positioning of the instrument device.

An exemplary method may include identifying, by a command interpreter in communication with a wireless controller, a reference location of a wireless controller; identifying, by the command interpreter, a second location of the wireless controller, and determining, based on the reference location and the second location, a sequence of instrument commands configured to adjust at least one of instrument rotation and instrument articulation angle.

DETAILED DESCRIPTION

Figure 1A:
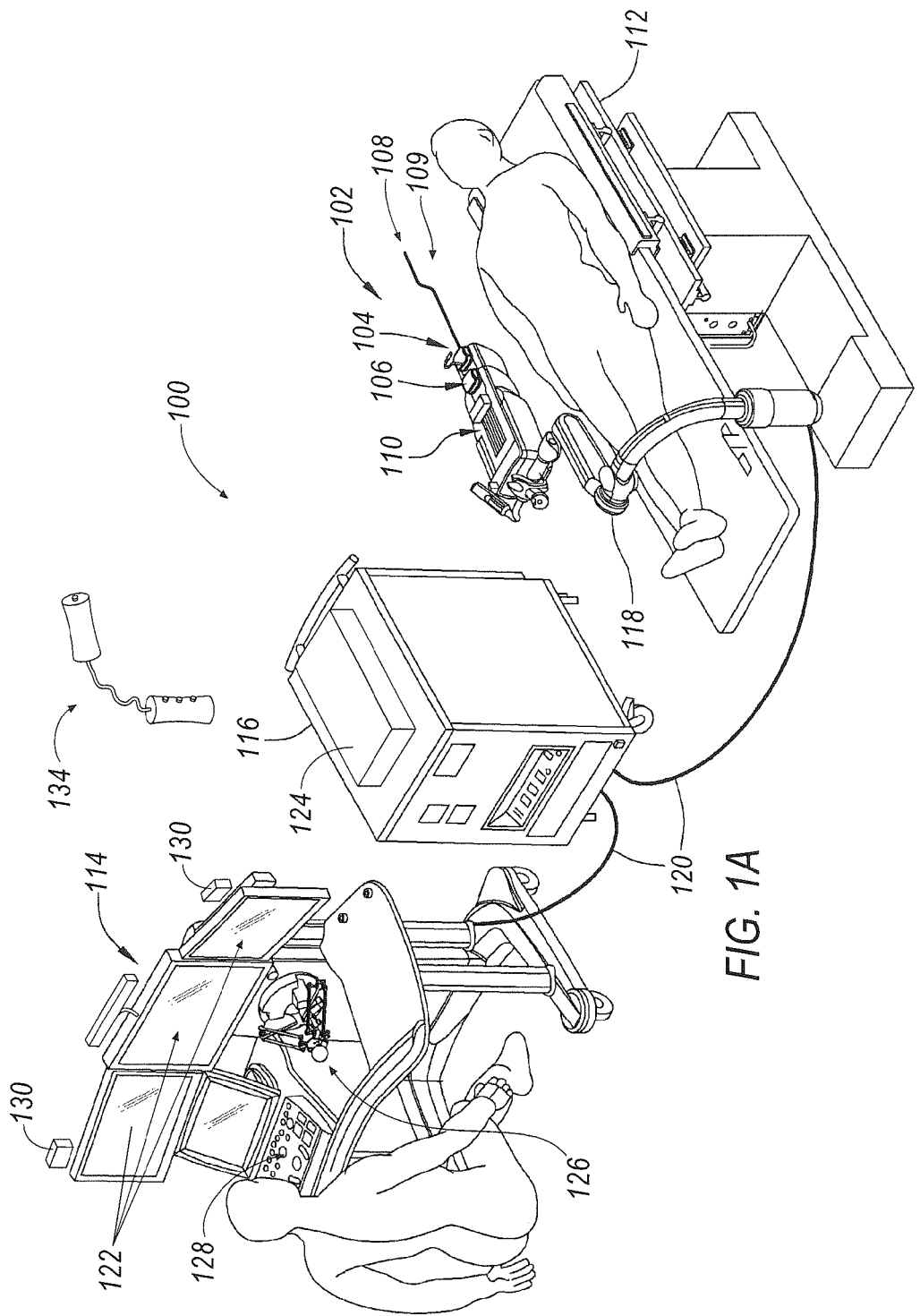
FIG. 1A illustrates an exemplary robotically controlled surgical system including a workstation.

Referring to FIG. 1A, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter 106" or "catheter instrument 106"). The catheter instrument 106 may further include a guide wire 108 (or "guide wire instrument 108") extendable beyond a distal end of the catheter instrument 106. Catheter assembly 102 is controllable using a robotic instrument driver 110 (generally referred to as "instrument driver"). During use, a patient is positioned on an operating table or surgical bed 112 (generally referred to as "operating table") to which robotic instrument driver 110 is coupled or mounted. In the illustrated example, system 100 includes an operator workstation 114, an electronics rack 116 and associated bedside electronics box (not shown), a setup joint mounting brace 118, and instrument driver 110. A surgeon is seated at operator workstation 114 and can monitor the surgical procedure, patient vitals, and control one or more catheter devices.

System components may be coupled together via a plurality of cables or other suitable connectors 120 to provide for data communication, or one or more components may be equipped with wireless communication components to reduce or eliminate cables 120. Communication between components may also be implemented over a network or over the interne. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

The operator workstation 114 may include one or more display monitors 122 configured to display a three dimensional object, such as a representation of the catheter instrument 106 and guide wire 108. The catheter instrument 106 and guide wire 108 may be displayed on the display monitors 122 within or relative to a three dimensional space, such as a body cavity or organ, e.g., a chamber of a patient's heart.

The operator workstation 114 may further provide various mechanisms for control of the catheter 106, guide wire 108, and display monitors 122. These mechanisms for control may provide input to a command interpreter 124, which may determine a sequence of commands to be provided to the catheter instrument 106 based on received input. In some cases, the command interpreter 124 may be implemented at least in part by one or more of the operator workstation 114, and electronics rack 116, while in other cases the command interpreter 124 may be implemented as a standalone component of the system.

Control of the medical instruments 109 (e.g., catheter 106 and/or guide wire 108) may be performed by way of an operator workstation 114 including a set of physical stationary controls, such as a joystick type controller 126 and a keyboard type input device 128. As one example, the catheter 106 may be controlled using the joystick type controller 126 allowing for steering of the distal tip of the guide catheter 106, while the guide wire 108 may be controlled using the keyboard type input device 128. Positioning of the catheter 106 may be viewable to an operator on the display monitor 122 according to X-ray fluoroscopy.

However, use of the stationary operator workstation 114 controls may cause the operator to be tied to a particular location in the operating room. Moreover, the operator workstation 114 may take up valuable real estate inside the operating room that may be otherwise used to store equipment, supplies, or provide better patient access.

Figure 1B:
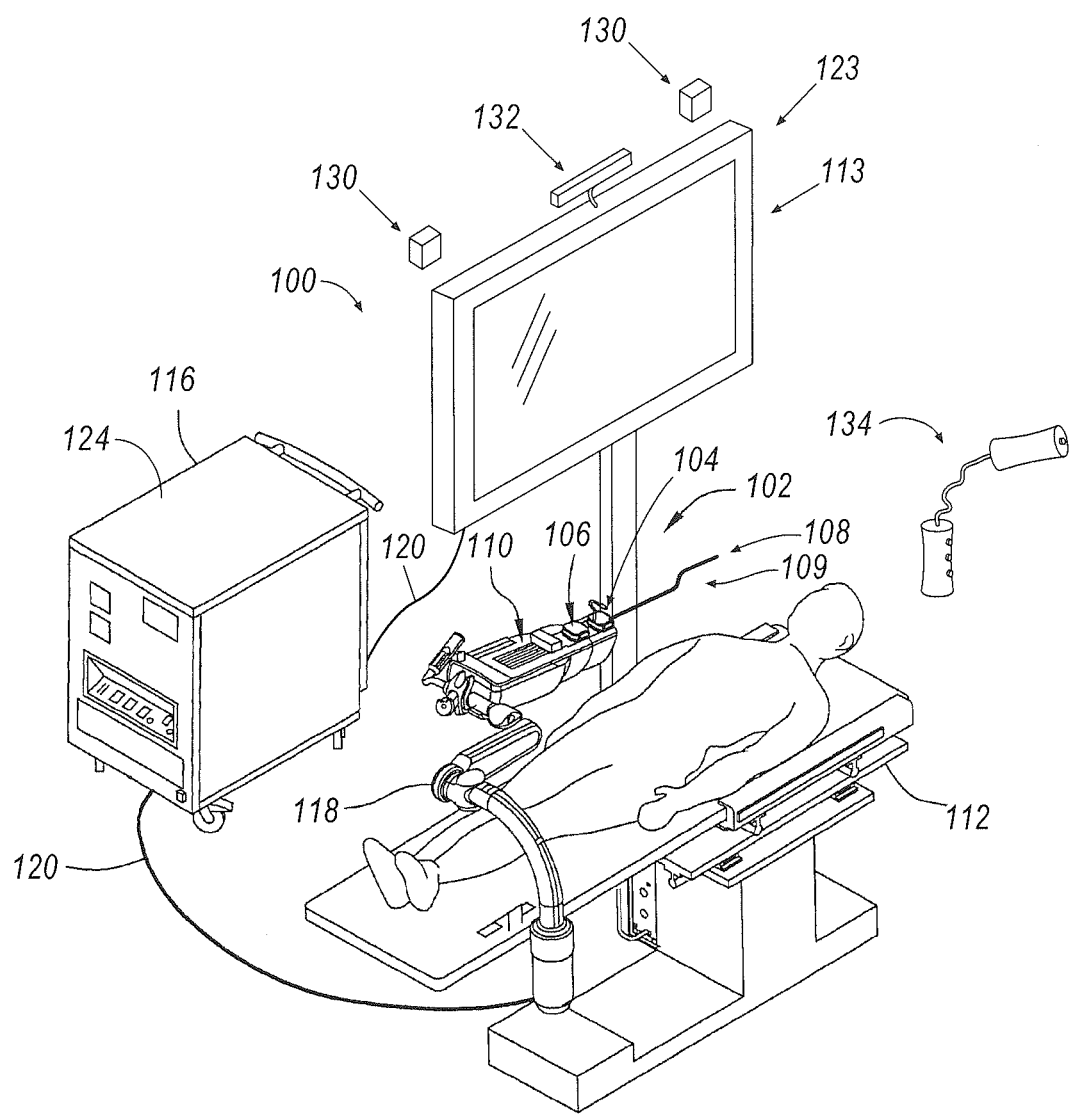
FIG. 1B illustrates an exemplary robotically controlled surgical system including a bedside monitor.

FIG. 1B illustrates an alternate robotically controlled surgical system 100 including a bedside monitor 123 instead of an operator workstation 114. Similar to the operator workstation 114, the bedside monitor 123 may include one or more display monitors 122 configured to display a three dimensional object, such as a representation of the catheter instrument 106 and guide wire 108. The bedside monitor 123 may take up significantly less space in the operating room due to its smaller size, in part a function of its reduced set of user interface controls. Thus, rather than being situated by the operator workstation 114 as illustrated in FIG. 1A, the operator instead may stand or otherwise work by the patient bedside.

The command interpreter 124 may be configured to use additional types of user interface device to augment or replace the physical controls of the operator workstation 114 or bedside monitor 123. For example, the command interpreter 124 may be configured to receive operator input from one or more of: a microphone array 130 configured to receive voice input such as spoken words, motion tracking sensors 132 configured to perform gesture recognition of operator movements, and wireless controllers 134 in wireless communication with the command interpreter 124. These additional types of user interface may be used by the command interpreter 124 to control the display monitor 122 of the operator workstation 114, as well as for controlling instrument 109 driving and instrument 109 shaping functionally of the robotically controlled catheter system 100.

The command interpreter 124 may be configured to perform voice recognition in order to implement a spoken user interface. The spoken user interface may be provided such that commands that may be performed using a physical user interface operator workstation 114 controls (e.g., touch screen, joystick type controller 126, keyboard type input device 128) may be replicated by way of voice commands. Use of voice commands accordingly allows an operator to control the system 100 without breaking sterility or withdrawing attention from the task at hand. As some exemplary voice commands, a voice command of "3D" may switch a main view on a display monitor 122 to a 3D view, a voice command of "Pan—Right" may pan a main image displayed by the display monitor 122 to the right (e.g., to center the view for the operator); a voice command of "Snapshot" may take a snapshot of the current view of the display monitor 122 for future reference; and a voice command of "use 035 wire" may select a wire type for use by the robotic catheter assembly 102.

In some examples, use of voice commands may be limited to non-driving functionality of the system 100. Moreover, due to the relatively inaccurate nature of voice control, in some examples voice commands may be limited to use for reversible configuration items with positive feedback when configuration is changed, typically on bedside monitor 123. Voice commands may also be used to facilitate confirmation of other actions, such as confirming that a particular instrument 109 movement should take place. In some examples, the command interpreter 124 may use speaker independent voice recognition in which voice commands may be accepted from any persons heard in the operating room, while in other examples the command interpreter 124 may be tuned to accept voice commands only from particular individuals (e.g., only from a physician). For robustness and due to the relative noise level in many operating rooms, an array of microphones 130 rather than a single microphone 130 may be used to reject noise sources and thereby increase voice recognition reliability.

The command interpreter 124 may be further configured to perform movement or gesture recognition in order to implement a non-verbal body-action user interface. Gesture recognition may include recognition of motions and positions of arms or other aspects of an operator. To distinguish between gesture input and other operator movements, in some cases gesture recognition may be performed on operator arms when positioned over the head of the operator. As an example of a gesture, the command interpreter 124 may use the motion tracking sensors 132 to identify an operator raising his or her hands and moving them from side to side to change a layout or rotate a 3D view on the display monitor 122. As another example, the command interpreter 124 may use the motion tracking sensors 132 to identify the locations or locations of the hands of an operator (e.g., hand orientation and hand position). This may be done to allow the command interpreter 124 to identify the positioning or movement of the hands intending to mimic a desired shape of the instrument 109, or to identify a desired motion to be performed on the instrument 109 by the robotic catheter assembly 102. Further, the command interpreter 124 may use the motion tracking sensors 132 to identify specific gestures, such as a waving of a hand from side to side, to facilitate entry into a gesture-based configuration mode that mimics properties of a currently displayed touch screen or display monitor 122 of the operator workstation 114.

The command interpreter 124 may be configured to use the motion tracking sensors 132 to identify operator gestures configured to set an instrument 109 to a particular desired shape or to drive the instrument 109. Different gestures may be associated with each of the three degrees of freedom, similar to the use of controls on a button or joystick 126 user interface device. Identifying an acted out gesture of the operator may accordingly cause the command interpreter 124 to perform an action on the instrument 109 in particular degree of freedom such as insert, roll, or articulate. As a further example, the command interpreter 124 may use the motion tracking sensors 132 to identify an arm of an operator as being used as an indication of an articulation angle and roll plane in order to perform relative or position-based driving of an instrument 109.

Similar to with voice commands, due to the inaccurate nature of gestures, actions without a reversible configuration may be confirmed by the command interpreter 124 to prevent undesired instrument 109 motion. In some cases, the command interpreter 124 may provide audible confirmation prompts combined with voice recognition to receive spoken confirmation of gesture actions identified by the command interpreter 124.

In some cases, simple gestures representing basic actions may be added together in a combinatory scheme to build more complicated sequences for controlling an instrument 109. Such a combinatory approach may be used to minimize the precision of motions required to provide for a given action. For example, a Jenkin's left shape may be input using a 180-degree articulation gesture, followed by a straight gesture, followed by a 45 degree articulation gesture.

In yet another scheme, a pair of 3D projection glasses may be worn by an operator. The projection glasses may be configured to overlay an image of the internals of a patient onto the patient. The glasses may also include a pair of cameras configured to track the hands or tools of the operator wearing the glasses. By pointing the hand or tool, the command interpreter 124 may be configured to recognize operator-provided commands to guide or pull the tip of the instrument 109 along in the patient.

The command interpreter 124 may be configured to use input received from a wireless controller 134 to provide another input mechanism for fine grain instrument 109 control. The input received from the wireless controller 134 may be used by the command interpreter 124 to control instrument 109 positioning or to control other aspects of the system 100. In some cases, the command interpreter 124 and wireless controller 134 may support bi-directional communications, such that the wireless controller 134 may be further configured to receive data sent from the command interpreter 124. As an example, the command interpreter 124 may be configured to provide confirmations to the wireless controller 134. As another example, the command interpreter 124 may be configured to provide haptic feedback commands to the wireless controller 134 to be performed by a haptic feedback module of the wireless controller 134.

Figure 2:
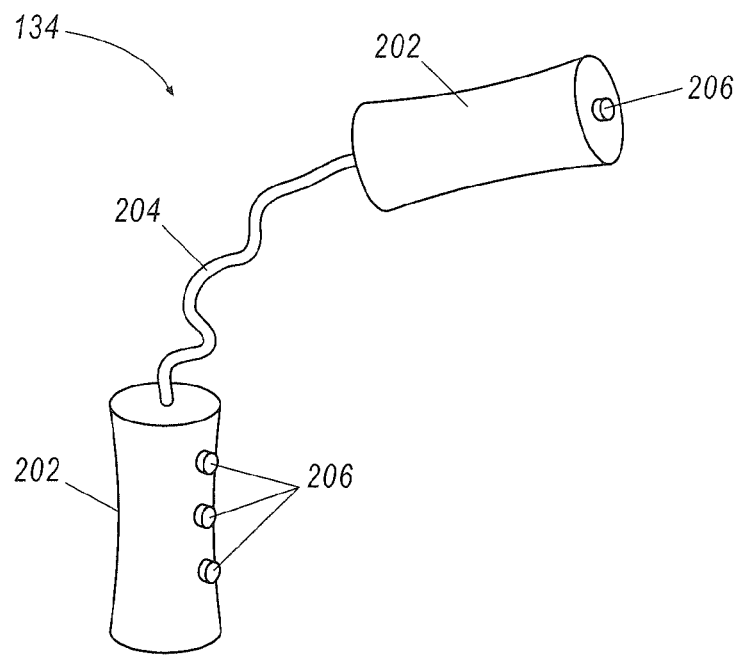
FIG. 2 illustrates an exemplary wireless controller device.

FIG. 2 illustrates an exemplary wireless controller 134. In some examples, to facilitate use by an operator, the wireless controller 134 may be shaped in a manner similar to that of an instrument 109. For instance, the wireless controller 134 may include two or more body elements 202 connected to one another according to a connection 204 to facilitate their controlled operation, such as in the manner that "nunchuks" may be connected to one another by a rope or chain connection 204. In other examples, the body elements 202 of the wireless controller 134 may be separate or separable without being fixed together by a connection 204.

In some examples, the multiple body elements 202 of the wireless controller 134 may communicate with one another according to a wired connection 204 between the body elements 202, while on other cases the multiple body elements 202 may communicate with one another wirelessly, separate from the connection 204. In further examples, the multiple body elements 202 of the wireless controller 134 may each be in communication with the command interpreter 124 directly.

To facilitate identifying positioning of the wireless controller 134, one or more of the body elements 202 of the wireless controller 134 may include location measurement devices configured to provide location information about the location of the body elements 202. The location information may include various types of information, such as one or more of: positional information, location information, acceleration information, and velocity information, as some examples. Exemplary devices to provide location information may include a three-axis gyroscope or a two-axis accelerometer. The devices may accordingly provide that a full range of motion may be distinguished and send on to the command interpreter 124 for interpretation into commands, e.g., to control medical instruments 109 such as the catheter 106 and/or guide wire 108.

In some examples, the wireless controller 134 may be draped in sterile packaging such that the wireless controller 134 may be set down within in the sterile field, while maintaining sterility. As another example, the wireless controller 134 may be implemented as a disposable controller, and may be opened from a sterile package and used a single time before being replaced.

The wireless controller 134 may also include a button 206 or other type of activation control configured to ensure that commands are only sent to the instrument 109 when explicitly desired by the user. For example, to provide for safe operation of the wireless controller 134 and to ensure clear movement beginnings and ends, the operator may indicate by way of a control 206 of the wireless controller 134 when a command action begins and/or ends. For example, the operator may press a button 206 on one or more of the body elements 202 of the wireless controller 134 to communicate to the command interpreter 124 that the operator is initiating a command sequence. The operator may also release the button 206 or press another button 206 to communicate to the command interpreter 124 that the operator is concluding the command sequence.

In other examples, rather than receiving explicit indications of when to capture location information related to the wireless controller 134 (e.g., according to receiving a button 206 press or other indication of when to capture the first or second location), the command interpreter 124 may instead continuously (or periodically) update with the location information of the wireless controller 134. For instance, the command interpreter 124 may identify the second location of the wireless controller 134 due to receiving an indication of operator movement of the wireless controller 134, or based on periodically polling the wireless controller 134 for location information.

Figure 3A:
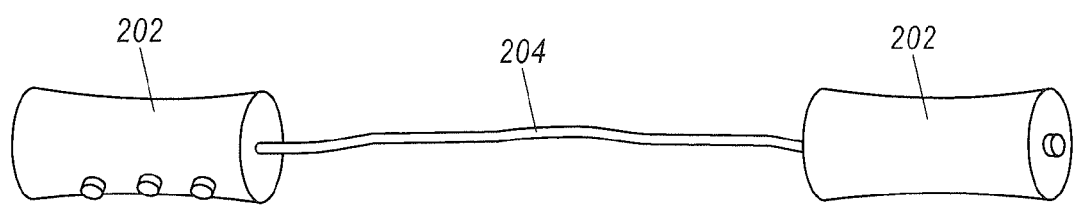
FIGS. 3A and 3B illustrate exemplary insertion or retraction command input by way of the wireless controller device.
Figure 3B:
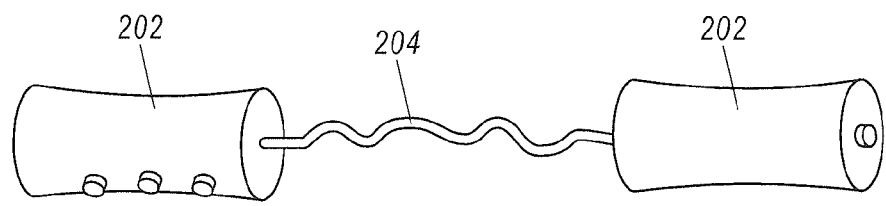

FIGS. 3A and 3B illustrate exemplary insertion or retraction command input by way of the wireless controller 134. As illustrated in FIG. 3A, two body elements 202 of a wireless controller 134 may be held a distance away from one another. Then as illustrated in FIG. 3B, the two body elements 202 of the wireless controller 134 may be moved toward one another. The body elements 202 may be configured to detect their motion toward or away from one another by way of included measurement functionality, such as by way of included location measurement devices. The command interpreter 124 may accordingly receive the location information from the two body elements 202 at the time as illustrated FIG. 3A and also at the time as illustrated in FIG. 3B, and may interpret the motion of the two body elements 202 toward one another as being indicative of an operator requesting an insert command. The command interpreter 124 may further identify a speed with which the two body elements 202 are moved together as being proportional to a speed of insertion requested by the operator.

As another example, an operator may indicate a retraction action using the wireless controller 134. For instance, the operator may first position the two body elements 202 of the wireless controller 134 near one another as illustrated in FIG. 3B, and may then move the two body elements 202 away from one another as illustrated in FIG. 3A. The command interpreter 124 may similarly receive location information from the two body elements 202 at the time as illustrated FIG. 3B and also at the time as illustrated in FIG. 3A, and may interpret the motion of the two body elements 202 away from one another as being indicative of an operator requesting a retract command.

As yet a further example, the reverse motions may be used to control the insert and retract. For example, the command interpreter 124 may interpret the two body elements 202 of the wireless controller 134 being moved toward one another as indicative of a retract action, and the two body elements 202 being moved away from one another as indicative of an insert action.

Figure 4:
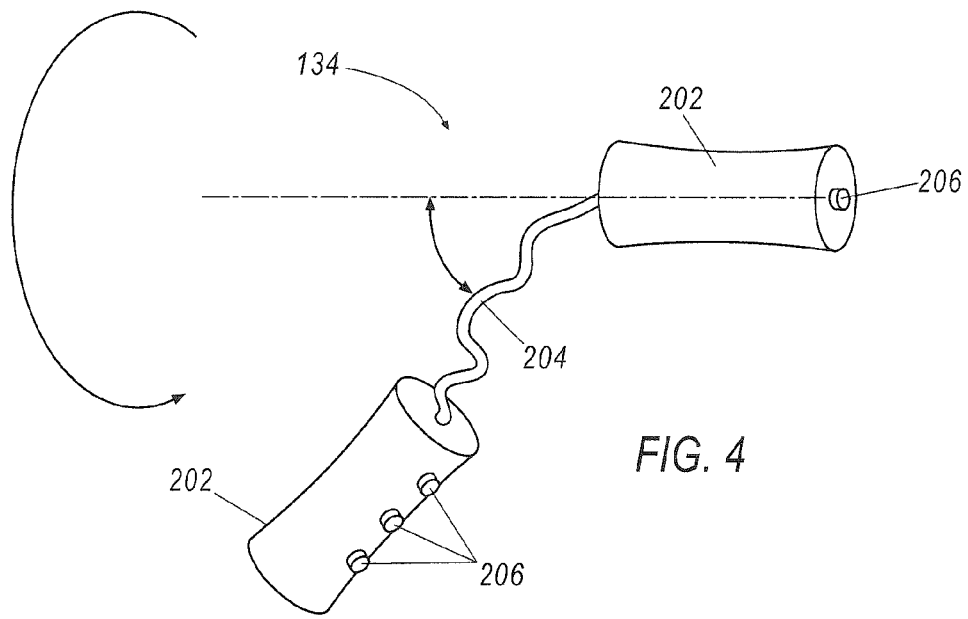
FIG. 4 illustrates exemplary rotation and articulation input by way of the wireless controller device.

FIG. 4 illustrates exemplary rotation and articulation command input by way of the wireless controller 134. For instance, an angle as defined between the two body elements 202 of the wireless controller 134 may be used to define an articulation angle of the instrument 109. Moreover, a plane defined by the orientation of the two body elements 202 of the wireless controller 134 may be used to define an angle of rotation of the instrument 109.

Figure 5:
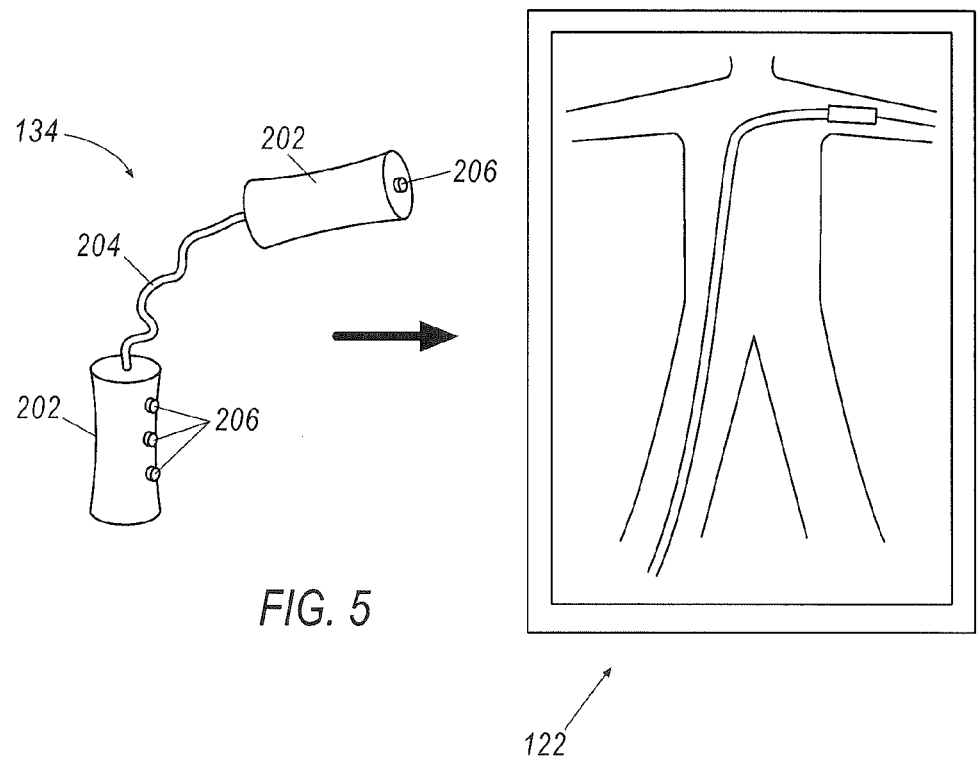
FIG. 5 illustrates exemplary command input by way of the wireless controller device.

FIG. 5 illustrates exemplary command input by way of the wireless controller 134. As illustrated, an operator may align the wireless controller 134 in a position consistent with the positioning of an instrument 109 displayed on a display monitor 122. For example, the wireless controller 134 may be held by an operator at an articulation angle and at an angle of rotation consistent with the illustrated positioning of the instrument 109. Once the wireless controller 134 is oriented consistent with the instrument 109 positioning, the operator may engage a button 206 on the wireless controller 134 to indicate a start of an input action. The command interpreter 124 may accordingly identify a reference articulation angle and a reference angle of rotation according to the orientation of the wireless controller 134. One benefit to this approach is that the operator may gain some instinctiveness (the orientation of the user interface correctly matching what is displayed) with respect to the properties of the instrument 109 by holding the wireless controller 134 in the orientation of the instrument 109.

The operator may further move the wireless controller 134 to a new desired orientation for the instrument 109. Once the desired location for the instrument 109 is reached, the operator may disengage the button 206 or press a button 206 to indicate the conclusion of the proposed movement. The command interpreter 124 may according identify a second articulation angle and second angle of rotation according to the new orientation of the wireless controller 134. In other examples, the command interpreter 124 may receive updated location information from the wireless controller 134 to determine the new desired orientation by polling or reception of messages indicative of location changes, without requiring an explicit additional action from the operator indicating when to capture the new location (e.g., by way of a button 206 press).

Based on the reference input and the second input, the command interpreter 124 may determine a sequence of one or more commands to be performed by the system 100 to move the instrument 109 to the desired position. For example, the command interpreter 124 may determine to perform an articulation command based on a change in articulation angle between the reference location and the second location. As another example, the command interpreter 124 may determine to perform a rotation command based on a change in rotation between the reference location and the second location. As yet a further example, the command interpreter 124 may determine to perform both an articulation command and also a rotation command.

Figure 6:
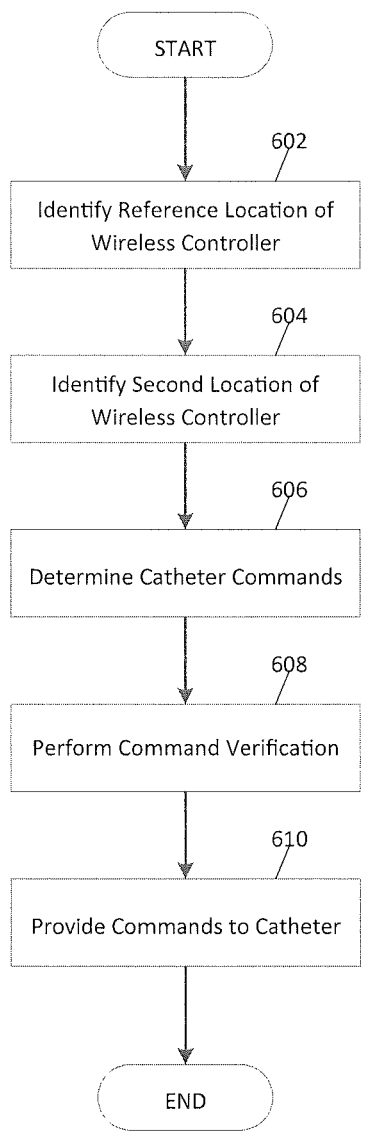
FIG. 6 illustrates an exemplary process for controlling a catheter using a wireless controller device.

FIG. 6 illustrates an exemplary process 600 for controlling an instrument 109 using a wireless controller 134. The process 600 may be performed by various devices, such as by a system 100 including a command interpreter 124 in communication with a wireless controller 134.

In block 602, the command interpreter 124 identifies a reference location of the wireless controller 134. For example, an operator may align the wireless controller 134 in a position consistent with that of a catheter 106 or other instrument 109 displayed on a display monitor 122. Once the wireless controller 134 is oriented consistent with the instrument 109 positioning, the operator may engage a button 206 on the wireless controller 134. The command interpreter 124 may accordingly receive location information from the two body elements 202, and may identify a reference rotation and articulation input according an angle defined between the two body elements 202 of the wireless controller 134 and a plane defined by the orientation of the two body elements 202 of the wireless controller 134.

In block 604, the command interpreter 124 identifies a second location of the wireless controller 134. For example, the operator may further move the wireless controller 134 to a new desired orientation for the instrument 109, and may disengage the button 206 or press a button 206 to indicate the conclusion of the proposed movement. The command interpreter 124 may according identify a second reference rotation and articulation input from the wireless controller 134. As another example, rather than requiring a button 206 press or other indication of when to capture the section location, the command interpreter 124 may instead continuously (or periodically) update with the location information of the wireless controller 134. For instance, the command interpreter 124 may identify the second location of the wireless controller 134 due to receiving an indication of operator movement of the wireless controller 134, or based on periodically polling the wireless controller 134 for location information.

In block 606, the command interpreter 124 determines a sequence of catheter commands to use to adjust a current catheter position. As an example, the command interpreter 124 may determine to perform an insert or retract command based on a change in distance between the two body elements 202 of the wireless controller 134. As another example, the command interpreter 124 may determine to perform an articulation command based on a change in articulation angle between the reference location and the second location, and/or to rotation command based on a change in rotation between the reference location and the second location.

In block 608, the command interpreter 124 receives verification of the sequence of catheter commands. For example, the command interpreter 124 may provide an audible prompt to the operator, and may receive voice confirmation to perform the sequence of catheter commands using voice recognition functionality of the command interpreter 124. As another example, the operator may accept the sequence of catheter commands according to gesture input or further input using the wireless controller 134, such as pressing a button 206.

In block 610, the command interpreter 124 provides the sequence of catheter commands to the instrument 109. Thus, the command interpreter 124 may cause the system 100 to perform the requested catheter 106 movements. After block 610, the process 600 ends.

Thus, by way of the command interpreter 124, the system 100 may provide for instrument 109 control using additional input sources, such as voice, gesture, and wireless controllers 134. As a result, an operator may no longer be tied to a particular location in the operating room. Moreover, the operator workstation 114 may be reduced in size or in some cases eliminated (e.g., in favor of a more space-efficient bedside monitor 123), thereby freeing up valuable real estate inside the operating room for use to store equipment, supplies, or provide better patient access.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein. The software executed by the operator workstation 114 or command interpreter 124 may be one such computer program product. In some example, the operator workstation 114 or command interpreter 124 software when executed by one or more processors may provide the operations described herein. Alternatively, the software may be provided as hardware or firmware, or combinations of software, hardware and/or firmware.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system configured to receive a user input and command operation of a robotic instrument driver based on the user input, the system comprising:
   a wireless controller for receiving a user input, the wireless controller comprising:
      a first body element including a first location measurement device,
      a second body element including a second location measurement device,
      a flexible connection physically connecting the first body element to the second body element while providing for movement of the first body element relative to the second body element in six degrees of freedom, and
      a wireless transmitter configured to provide location information from the first location measurement device and the second location measurement device; and
   a command interpreter in wireless communication with the wireless controller, the command interpreter configured to:
      identify a reference location of the first body element relative to the second body element from first location information received from the wireless controller,
      identify a second location of the first body element relative to the second body element from second location information received from the wireless controller,
      detect, based on the reference location and the second location, motion of the first body element relative to the second body element, and
      determine, based on the motion of the first body element relative to the second body element, a sequence of instrument commands configured to adjust a position or orientation of an instrument in accordance with the user input.

2. The system of claim 1, wherein the sequence of instrument commands is configured to adjust at least one of instrument rotation, instrument articulation angle, or instrument insertion amount.

3. The system of claim 1, wherein the instrument is at least one of a catheter or a guide wire.

4. The system of claim 1, wherein the reference location identifies a reference rotation according to an angle defined between the first and second body elements of the wireless controller and a reference articulation angle according to a plane defined by an orientation of the first and second body elements of the wireless controller.

5. The system of claim 1, wherein the detected motion of the first body element relative to the second body element comprises at least one of a change in instrument rotation as compared to the reference location, a change in articulation angle as compared to the reference location, or a change in distance between the first and second body elements of the wireless controller as compared to the reference location.

6. The system of claim 1, wherein the command interpreter is further configured to:
   receive a user interface action configured to cause the command interpreter to identify the reference location; and
   receive a second user interface action configured to cause the command interpreter to identify the second location.

7. The system of claim 1, wherein the command interpreter is further configured to:
   receive operator confirmation of the determined sequence of instrument commands; and
   provide the determined sequence of instrument commands to an instrument driver to perform the requested instrument position adjustment.

8. A method of translating a user input into a command for a robotic instrument driver, the method comprising:
   receiving a user input at a wireless controller, the wireless controller comprising a first body element, a second body element, and a flexible connection physically connecting the first body element to the second body element while providing for movement of the first body element relative to the second body element in six degrees of freedom;
   identifying, by a command interpreter in wireless communication with the wireless controller, a reference location of the first body element relative to the second body element;
   identifying, by the command interpreter, a second location of the first body element relative to the second body element,
   detecting, based on the reference location and the second location, motion of the first body element relative to the second body element, and
   determining, based on the motion of the first body element relative to the second body element, a sequence of instrument commands for commanding an instrument driver to adjust at least one of instrument rotation, instrument articulation angle, or instrument insertion amount of an instrument.

9. The method of claim 8, wherein the instrument is at least one of a catheter or a guide wire.

10. The method of claim 8, wherein identifying a reference location comprises identifying a reference rotation according to an angle defined between the first and second body elements of the wireless controller and a reference articulation angle, according to a plane defined by an orientation of the first and second body elements of the wireless controller.

11. The method of claim 8, wherein detecting motion of the first body element relative to the second body element comprises identifying at least one of a change in instrument rotation, a change in articulation angle, or a change in distance between body elements of the wireless controller.

12. The method of claim 8, further comprising:
   receiving a user interface action configured to cause the command interpreter to identify the reference location; and
   receiving a second user interface action configured to cause the command interpreter to identify the second location.

13. The method of claim 8, further comprising:
   receiving operator confirmation of the determined sequence of instrument commands; and
   providing the determined sequence of instrument commands to the instrument driver to perform the requested instrument position adjustment.

* * * * *